United States Patent [19]

Kobayashi et al.

[11] Patent Number: 5,169,955

[45] Date of Patent: Dec. 8, 1992

[54] PROCESS FOR PRODUCING 2-HYDROXYQUINOXALINE DERIVATIVES

[75] Inventors: Hisabumi Kobayashi, Ageo; Hiroshi Maruyama, Tokyo; Shuji Kawata, Yono; Sadahiko Noda, Omiya, all of Japan

[73] Assignee: Nippon Kayaku Kabushiki Kaisha, Tokyo, Japan

[21] Appl. No.: 658,756

[22] Filed: Feb. 21, 1991

[30] Foreign Application Priority Data

Mar. 1, 1990 [JP] Japan ................ 2-47170
Oct. 30, 1990 [JP] Japan ................ 2-290897

[51] Int. Cl.$^5$ .......................... C07D 241/44
[52] U.S. Cl. .................... 544/354; 564/305; 564/442
[58] Field of Search ........................ 544/354

[56] References Cited

U.S. PATENT DOCUMENTS

| | | | |
|---|---|---|---|
| 2,537,871 | 1/1951 | Wolf | 544/354 |
| 3,928,350 | 12/1975 | Nottke | 544/354 |
| 4,264,600 | 4/1981 | Abdulla | 544/354 |
| 4,450,271 | 5/1984 | Su et al. | 544/354 |
| 4,620,003 | 10/1986 | Ishikura | 544/354 |
| 4,814,444 | 3/1989 | Malz, Jr. et al. | 544/354 |

FOREIGN PATENT DOCUMENTS

| | | | |
|---|---|---|---|
| 728649 | 2/1966 | Canada | 544/354 |
| 130977 | 8/1982 | Japan | 544/354 |

OTHER PUBLICATIONS

Abstract for JP130977 (Aug. 13, 1982).
Patent Abstracts of Japan, vol. 6, No. 227 (C-134)(1105) Nov. 12, 1982 & JP-A-57 130 977 (Nippon Gosei).

*Primary Examiner*—John M. Ford
*Assistant Examiner*—E. Bernhardt
*Attorney, Agent, or Firm*—Nields & Lemack

[57] ABSTRACT

A process for producing a 2-hydroxyquinoxaline which may be substituted with one or more substituents selected from the group consisting of halogen, lower alkyl and lower alkoxy, which comprises reacting o-phenylenediamine which may be substituted with one or more substituents selected from the group consisting of halogen, lower alkyl and lower alkoxy with glyoxylic acid in a lower aliphatic alcohol solvent without using a catalyst is disclosed. By the process according to the present invention, the 2-hydroxyquinoxaline derivatives can be obtained at a high purity and a high yield without using any catalyst.

4 Claims, No Drawings

PROCESS FOR PRODUCING 2-HYDROXYQUINOXALINE DERIVATIVES

DETAILED DESCRIPTION OF THE INVENTION

The present invention relates to a process for producing 2-hydroxyquinoxaline derivatives useful as an intermediate product for the production, for example, of agricultural chemicals (for example quinalphos), medicines and dyes.

A method of reacting glyoxylic acid and o-phenylenediamine in a dimethylformamide solvent at a temperature of −10° C. has been reported (C.A. 88, 121243 g (1978)). Further, a method of reacting glyoxylic acid and o-phenylenediamine in a lower aliphatic alcohol in the presence of a formic acid or acetic acid catalyst is described in Japanese Patent Publication (KOKOKU) No. 1-61105(1989).

The method of using the dimethylformamide solvent is not satisfactory to be practiced in an industrial scale since the solvent is expensive and has a high boiling point and, accordingly, due to the reasons of requiring a special reaction device or increased burden upon recovery of the solvent. Further, the method of using the formic acid or acetic acid catalyst involves a difficulty in recovering a pure solvent (lower aliphatic alcohol) not containing said catalyst and recovering the acid catalyst in a filtrate after the filtration of crystals of 2-hydroxyquinoxaline derivatives. In this way, the conventional methods have fatal drawbacks in view of industrial production.

Accordingly, it has been desired for the development of a production process without lowering the yield and with easy recovery of the solvent.

The present inventors have found a process for producing 2-hydroxyquinoxaline which may be substituted with one or more substituents selected from the group consisting of halogen, lower alkyl and lower alkoxy (hereinafter referred to as "2-hydroxyquinoxaline derivatives" which include 2-hydroxyquinoxaline per se), without using an acid catalyst and at a higher yield than in the prior art by gradually little by little adding o-phenylenediamine which may be substituted with one or more substituents selected from the group consisting of halogen, lower alkyl and lower alkoxy (hereinafter referred to as "o-phenylenediamine derivatives" which include o-phenylenediamine per se) into a solution of glyoxylic acid in a lower aliphatic alcohol solvent and reacting the o-phenylenediamine derivative and glyoxylic acid.

In the present invention, the solvent can be recovered easily since no acid catalyst is used and, thus, the object can be attained with an industrial advantage.

As the lower aliphatic alcohol solvent used in the present invention, there can be mentioned, for example, methanol, ethanol, propanol, isopropanol, butanol and a solvent mixture comprising said alcohol(s) and water.

In the case of the mixed solvent, preferred are those containing water upto 0.5 part by weight to 1 part by weight of alcohol and, preferably, water upto 0.3 part by weight to 1 part by weight of alcohol. Although there is no particular restriction for the amount of the solvent used, it is preferably from 500 to 1000 ml based on one mol of o-phenylenediamine derivative since the reaction rate becomes slow if a great amount is used.

The o-phenylenediamine derivatives used in the present invention include o-phenylenediamine per se and o-phenylenediamine which is substituted with one or more substituents selected from the group consisting of halogen, lower alkyl and lower alkoxy. Preferred substituents may include chlorine, $C_1$-$C_4$ alkyl group and $C_1$-$C_4$ alkoxy group. As the preferred example of the o-phenylenediamine derivatives, there can be mentioned o-phenylenediamine, 4,5-dichloro-o-phenylenediamine, 4,5-dimethyl-o-phenylenediamine and 4,5-dimethoxy-o-phenylenediamine.

The 2-hydroxyquinoxaline derivatives produced according to the process of the present invention include 2-hydroxyquinoxaline per se and 2-hydroxyquinoxaline which is substituted with one or more substituents selected from the group consisting of halogen, lower alkyl and lower alkoxy. Preferred substituents may include chlorine, $C_1$-$C_4$ alkyl group and $C_1$-$C_4$ alkoxy group. As the preferred example of the 2-hydroxyquinoxaline derivatives, there can be mentioned 2-hydroxyquinoquixaline, 2-hydroxy-6,7-dichloroquinoxaline, 2-hydroxy-6,7-dimethylquinoxaline and 2-hydroxy-6,7-dimethoxyquinoxaline.

Glyoxylic acid can be used in the form of crystals and aqueous solutions and, although there is no particular restrictions for the amount of use, it is preferably used by from 0.8 to 1.3 molar times based on the o-phenylenediamine derivative.

The reaction is carried out at a temperature from −20° to 50° C., preferably, from −5° to 20° C., and more preferably, from −2° to 5° C.

In the present invention, the o-phenylenediamine derivative in the form of crystals or solution dissolved in a solvent (preferably, the lower aliphatic alcohol solvent described above) is added little by little. Since evolution of heat occurs in this case, addition is conducted while maintaining the above-mentioned temperature. The time for addition is preferably from 1 to 6 hours although it depends on the reaction temperature or other conditions. In that case, the amount of the o-phenylenediamine derivative to be added per unit time (per one minute or per one hour) is preferably maintained constant.

Since highly pure products can be obtained by the process according to the present invention, purification such as treatment with activated carbon or recrystallization is not necessary.

According to the present invention, the desired products can be obtained at a high purity and a high yield by gradually adding to react the o-phenylenediamine derivative into a solution of glyoxylic acid in the lower alcohol solvent. In addition, since no acid catalyst is used, the solvent can be recovered easily to enable industrially advantageous production.

The effect of the present invention will now be illustrated more specifically in the following examples but the invention is not restricted by the examples.

EXAMPLE 1

97.2 g of 40% glyoxylic acid were charged into a reaction vessel, to which 250 ml of methanol were added and cooled to 0° to −4° C. under stirring.

55.2 g of crystals of o-phenylenediamine (98% purity) were gradually added at the same temperature as above over 2 hours. Further, the reaction mixture was stirred at that temperature for 2 hours to complete the reaction.

After the completion of the reaction, the product was filtered at that temperature, washed with 50% methanol and then dried, to obtain 66.5 g of the desired product (2-hydroxyquinoxaline).

When the purity was determined by the internal standard method using high performance liquid chromatoography it was 99.6%. The yield based on o-phenylenediamine was 90.6%. The melting point of the product was 268° to 270° C.

EXAMPLE 2

The same reaction and post-treatment as in Example 1 were conducted by using ethanol instead of methanol to obtain 66.3 g of the desired product (2-hydroxyquinoxaline). The purity was 99.4% and the yield was 90.2%. The melting point was 268° to 270° C.

REFERENCE EXAMPLE 1

55.2 g of o-phenylenediamine (98% purity) were charged in a reaction vessel to which 250 ml of methanol were added and cooled to 4° to 6° C. 97.2 g of 40% glyoxylic acid were added dropwise thereto at that temperature for 2 hours. After the addition, the reaction mixture was stirred at that temperature for 30 min and, thereafter, the temperature was elevated to 50° C. and stirring was further conducted at that temperature for one hour. The reaction mixture was cooled to a room temperature, filtered and then dried, to obtain 56.0 g of the desired product (2-hydroxyquinoxaline). The purity was 93.4%, and the yield was 71.6%. The melting point was 266° to 268° C.

REFERENCE EXAMPLE 2

After adding methanol in Reference Example 1, 5 ml of acetic acid was added and then reaction and post-treatment were conducted in the same way as in Reference Example 1 to obtain 60.9 g of the desired product (2-hydroxyquinoxaline). The purity was 96.0% and the yield was 80.0%. The melting point was 267° to 269° C.

EXAMPLE 3

2.7 liter of 80% (w/w) aqueous methanol were charged in a reaction vessel and then cooled to −2° to 2° C. under stirring, to which 1.4 kg of 50% aqueous glyoxylic acid solution were added gradually. Further, a solution prepared by dissolving 0.98 kg of o-phenylenediamine into 4.5 liter of 80% (w/w) aqueous methanol solution were added gradually over three hours. Further, the reaction mixture was stirred at that temperature for 0.5 hours to complete the reaction. After the completion of the reaction, pH value was adjusted to 6.5 by using an aqueous alkali and the product was filtered. After washing with 1.0 liter of 80% (w/w) aqueous methanol, drying was applied to obtain 1223 g of the desired product (2-hydroxyquinoxaline). When the purity was determined, it was 99.6%. The yield was 93% based on o-phenylenediamine. When methanol was recovered from the liquid filtrate by means of simple distillation, 93% was recovered.

EXAMPLE 4

Using 4,5-dichloro-o-phenylenediamine in stead of o-phenylenediamine in Example 1, 4,5-dichloro-2-hydroxyquinoxaline was obtained by the same manner as in Example 1. The melting point was 343° C.

EXAMPLE 5

5.9 liter of 80% (w/w) aqueous methanol were charged in a reaction vessel and then cooled to −2° to 2° C. under stirring, to which 1.53 kg of 50% aqueous glyoxylic acid were added gradually. Further, 0.98 kg of o-phenylenediamine was added gradually thereto at that temperature over 2 hours. Further, the reaction mixture was stirred for 30 minutes to complete the reaction.

After the stirring, the product was filtered at the same temperature, washed with 80% of aqueous methanol of −2° to 2° C. and dried to obtain 1.309 kg of 2-hydroxyquinoxaline. The purity was 99.5% and the yield was 99.0% (based on o-phenylenediamine).

What is claimed is:

1. A process for producing a 2-hydroxyquinoxaline the benzo ring of which may be substituted with one or more substituents selected from the group consisting of halogen, lower alkyl and lower alkoxy, which comprises reacting o-phenylenediamine which may be substituted with one or more substituents selected from the group consisting of halogen, lower alkyl and lower alkoxy with glyoxylic acid in a lower aliphatic alcohol solvent selected from the group consisting of methanol, ethanol, n-propanol and isopropanol without using a catalyst, the o-phenylenediamine derivative being added gradually little by little into a solution of glyoxylic acid in the lower aliphatic alcohol solvent.

2. A process as defined in claim 1, wherein the reaction is carried out within a range from −5° to 20° C.

3. A process as defined in claim 1, wherein the reaction is carried out within a range from −2° to 5° C.

4. A process as defined in claim 1, 2 or 3, wherein the o-phenylenediamine derivative is added to the solution of glyoxylic acid in the lower aliphatic alcohol solvent over a period of 1 to 6 hours.

* * * * *